United States Patent [19]

Yamamoto et al.

[11] 4,146,717
[45] Mar. 27, 1979

[54] NITROQUINAZOLINONE COMPOUNDS HAVING ANTIVIRAL PROPERTIES

[75] Inventors: Michihiro Yamamoto, Toyonaka; Shigeaki Morooka, Takarazuka; Masao Koshiba, Takarazuka; Toshiaki Komatsu, Takarazuka; Hiroshi Noguchi, Takarazuka; Shigeho Inaba, Takarazuka; Hisao Yamamoto, Nishinomiya, all of Japan

[73] Assignee: Sumitomo Chemical Company, Limited, Osaka, Japan

[21] Appl. No.: 454,284

[22] Filed: Mar. 25, 1974

Related U.S. Application Data

[63] Continuation-in-part of Ser. No. 242,241, Apr. 7, 1972, abandoned.

[51] Int. Cl.² ............................................. C07D 239/82
[52] U.S. Cl. .............................. 544/284; 424/248.51; 424/248.54; 424/251; 544/119; 544/286
[58] Field of Search .................... 260/25 QB, 256.4 Q, 260/256.5 R; 544/284, 286

[56] References Cited

U.S. PATENT DOCUMENTS

| | | | |
|---|---|---|---|
| 3,812,118 | 5/1974 | Yamamoto et al. | 260/247.1 |
| 3,829,420 | 8/1974 | Inaba et al. | 260/25 QB |

OTHER PUBLICATIONS

Newsletter-St. Jude Children's Research Hospital, vol. 10, No. 1, (1978).
Inaba et al. – CA78, 72190v (1973).

*Primary Examiner*—Raymond V. Rush
*Attorney, Agent, or Firm*—Stevens, Davis, Miller & Mosher

[57] ABSTRACT

Viral infections caused by viruses which belong to, e.g. Pox, Herpes, Adeno, Myxo, Paramyxo groups are controlled by administering an effective amount of quinazoline derivatives of the formula

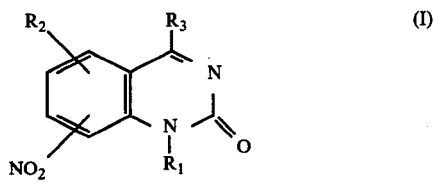

wherein $R_1$ is cyclo, $C_3$-$C_8$ alkyl, cyclo $C_3$-$C_8$ alkyl $C_1$-$C_4$ alkyl, $C_1$-$C_4$ alkoxy $C_1$-$C_4$ alkyl, $C_2$-$C_5$ alkenyloxy $C_1$-$C_4$ alkyl, $C_1$-$C_4$ alkylthio $C_1$-$C_4$ alkyl, polyhalo $C_1$-$C_4$ alkyl, a group of the formula

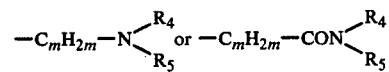

(wherein m is an integer of 1 to 3; and $R_4$ and $R_5$ are individually $C_1$-$C_4$ alkyl, and may form together with the adjacent nitrogen atom an unsubstituted or $C_1$-$C_4$ alkyl substituted 3 to 6 membered saturated heterocyclic ring, which may contain another nitrogen or oxygen atom) or a group of the formula $-C_nH_{2n}-R_6$ (wherein n is 0 or an integer of 1 to 3; and $R_6$ is a phenyl group, a substituted phenyl group or an aromatic or non-aromatic 3 to 6 membered heterocyclic ring which contains one or two hetero atoms selected from the group consisting of nitrogen, oxygen and sulfur atom, and may be optionally substituted by one or two $C_1$-$C_4$ alkyl, and further, those substituents on adjacent carbon atoms may be joined to form a benzene or cyclohexane ring); $R_2$ is hydrogen, halogen, $C_1$-$C_4$ alkyl, $C_1$-$C_4$ alkoxy, $C_1$-$C_4$ alkylthio, $C_1$-$C_4$ alkylsulfonyl, trifluoromethyl or nitro; and $R_3$ is phenyl, substituted phenyl, cyclo $C_3$-$C_6$ alkyl, pyridyl, furyl, nitrofuryl, thienyl, nitrothienyl, methylthienyl or pyrimidinyl.

7 Claims, No Drawings

NITROQUINAZOLINONE COMPOUNDS HAVING ANTIVIRAL PROPERTIES

CROSS REFERENCE TO THE RELATED APPLICATION

This application is a continuation-in-part of application Ser. No. 242,241 filed on Apr. 7, 1972, now abandoned.

This invention relates to nitroquinazolinones possessing antiviral activity.

More particularly, the invention pertains to a method and compositions for controlling viral infections in animals by employing the above compounds. The invention also relates to novel 2(1H)-quinazolinones and methods of preparing the same.

The nitroquinazolinones of the present invention may be represented by the formula,

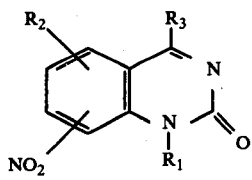

wherein $R_1$ is a cyclo $C_3$–$C_8$ alkyl group, a cyclo $C_3$–$C_8$ alkyl $C_1$–$C_4$ alkyl group, a $C_1$–$C_4$ alkoxy $C_1$–$C_4$ alkyl group, a $C_2$–$C_5$ alkenyloxy $C_1$–$C_4$ alkyl group, a $C_1$–$C_4$ alkylthio $C_1$–$C_4$ alkyl group, a polyhalo $C_1$–$C_4$ alkyl group, a group of the formula

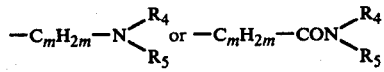

(wherein m is an integer of 1 to 3; and $R_4$ and $R_5$ are individually a $C_1$–$C_4$ alkyl group, and may form together with the adjacent nitrogen atom an unsubstituted or $C_1$–$C_4$ alkyl substituted 3 to 6 membered saturated heterocyclic ring, which may contain another nitrogen or oxygen atom) or a group of the formula —$C_nH_{2n}$—$R_6$ (wherein n is 0 or an integer of 1 to 3; and $R_6$ is a phenyl group, a substituted phenyl group or an aromatic or non-aromatic 3 to 6 membered heterocyclic ring which contains one or two hetero atoms selected from the group consisting of nitrogen, oxygen and sulfur atom, and may be optionally substituted by one or two $C_1$–$C_4$ alkyl groups, and further, those substituents on adjacent carbon atoms may be joined to form a benzene or cyclohexane ring); $R_2$ is a hydrogen atom, a halogen atom, a $C_1$–$C_4$ alkyl group, a $C_1$–$C_4$ alkoxy group, a $C_1$–$C_4$ alkylthio group, a $C_1$–$C_4$ alkylsulfonyl group, a trifluoromethyl group or a nitro group; and $R_3$ is a phenyl group, a substituted phenyl group, a cyclo $C_3$–$C_6$ alkyl group, a pyridyl group, a furyl group, a nitrofuryl group, a thienyl group, a nitrothienyl group, a methylthienyl group or a pyrimidinyl group.

In the compounds represented by the formula [I], the term "alkyl" means both straight and branched chain aliphatic hydrocarbon radicals, and the $C_1$–$C_4$ alkyl includes, for example, methyl, ethyl, n-propyl, isopropyl, n-butyl, isobutyl and tertiary-butyl; the $C_1$–$C_4$ alkoxy includes, for example, methoxy, ethoxy, n-propoxy, isopropoxy, n-butoxy and tertiary-butoxy; the $C_1$–$C_4$ alkylthio includes, for example, methylthio, ethylthio, isopropylthio and butylthio; the term "halogen" comprehends all halogens (i.e. fluorine, chlorine, bromine and iodine); the cycloalkyl includes, for example, cyclopropyl, cyclobutyl, cyclopentyl, cyclohexyl, cycloheptyl and cyclooctyl; the $C_2$–$C_5$ alkenyl includes, for example, vinyl, allyl, methallyl, butenyl and crotyl; the polyhaloalkyl includes, for example, 2,2,2-trifluoroethyl, 2,2,2-trichloroethyl, 2-chloro-2,2-difluoroethyl and 2,2,3,3,3-pentafluoropropyl; the substituted phenyl includes, for example, halophenyl, $C_1$–$C_4$ alkylphenyl, $C_1$–$C_4$ alkoxyphenyl and nitrophenyl; the heterocyclic ring formed by $R_4$ and $R_5$ together with the adjacent nitrogen atom includes, for example, aziridine, azetidine, pyrrolidine, piperidine, piperazine and morpholine; the heterocyclic group represented by $R_6$ includes, for example, aziridinyl, azetidinyl, pyrrolidinyl, piperidyl, morpholinyl, epoxyethyl, 1,3-epoxypropyl, tetrahydrofuryl, tetrahydropyranyl, 1,3-dioxacyclohexyl, 1,4-dioxacyclohexyl, tetrahydrothienyl, thiacyclohexyl, pyrrolyl, pyrazolyl, imidazolinyl, pyridyl, pyrimidinyl, pyrazinyl, furyl, pyranyl, thienyl, oxazolyl, isoxazolyl, thiazolyl, oxazinyl, indolyl, benzofuranyl, benzoxazolyl and 1,4-benzodioxanyl and $C_1$–$C_4$ alkyl substituted derivatives thereof. The alkylene group represented by $C_nH_{2n}$ or $C_mH_{2m}$ includes straight chain or branched chain alkylene such as methylene, ethylene, 1-methylethylene, 2-methylethylene or trimethylene.

There have been already known some of the compounds of the formula [I] having anti-inflammatory and analgesic activities (Brit. Pat. Nos. 1,251,600 and 1,313,789). It was found, to our surprise that the quinazolinones of the formula [I] have remarkably potent antiviral activity for the first time. Antiviral activity of the compounds of the formula [I] or analogous compounds thereof has not been ever reported in any literature.

Preferred compounds falling within the formula [I] have $R_1$ as a group of the formula —$C_{n'}H_{2n'}$—R (wherein n' is 0 or 1; and R is phenyl, substituted phenyl, cyclo $C_3$–$C_8$ alkyl, or 5 to 6 membered aromatic or non-aromatic heterocyclic ring which contains one hetero atom selected from the group consisting of nitrogen, oxygen and sulfur atom); $R_2$ is hydrogen; and $R_3$ is phenyl, substituted phenyl, cyclohexyl or thienyl.

Among the compounds of the formula [I], the quinazolinones represented by the formula,

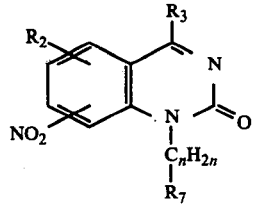

wherein $R_2$, $R_3$ and n are as defined above; and $R_7$ is an aromatic or non-aromatic 3 to 6 membered heterocyclic ring which contains one or two hetero atoms selected from the group consisting of nitrogen, oxygen and sulfur atom, and may be optionally substituted by one or two $C_1$–$C_4$ alkyl groups, and further, those substituents on adjacent carbon atoms may be joined to form a benzene or cyclohexane ring, are novel.

Accordingly, an object of the present invention is to provide a method for controlling viral infections comprising administering to animals at least one compound of the formula [I]. Another object of the present invention is to provide an antiviral composition comprising at least one compound of the formula [I] and a pharmaceutical carrier. A further object of the present invention is to provide novel quinazolinones of the formula [II] excellent particularly in antiviral action. Other objects will be apparent from the following disclosure and discussion.

As reviewed by L. Weinstein in "Pharmacological Basis of Therapeutics" (L. S. Goodman & A. Gilman, McMillan Company) p. 1305-7 (1970), very few agents have been found to have clinical applicability for antiviral drug although the search for substances that might be of use in the management of viral infections has been long and intensive. Idoxuridine, Amantadine and Methisazone, synthetic antivirals for clinical use, are described in said text. Idoxuridine is only effective against DNA type viruses such as herpes simplex and vaccinia, and it can only be used by topical application because of its toxicity.

The only clinical use of Amantadine is for the prevention of $A_2$ influenza virus infection.

As it has severe side effect on central nervous system, great care must be taken in administration.

Methisazone is considered to be a promising antiviral drug on a small pox infection. But Weinstein described about it in the aforementioned text as follows: "The place of Methisazone in the therapy of infections produced by the pox group of viruses is unsettled, and the drug is still in the investigational stage". Further undesirable side effects of Methisazone noted up to the present have been severe vomiting, dermatitis and jaundice.

The compounds of the formula [I] may be employed to control, namely to treat and prevent viral infections caused by DNA type viruses such as Pox group and RNA type viruses such as Myxo group. They are also used to treat abnormal conditions caused by vaccination of live attenuated viruses.

More particularly, these compounds have exhibited remarkable antiviral activities against vaccinia, influenza and parainfluenza viruses.

For example, these compounds can inhibit the vaccinia virus multiplication in very low concentration in tissue culture method using chick embryo fibroblast or HeLa cell. Furthermore they are negligibly cytotoxic. The present compound No. 3 cited in Table VIII, for example, has the value of 0.1 μg/ml in the minimum inhibitory concentration (MIC) and 100 μg/ml in the minimum toxic concentration (MTC). Therefore a chemotherapeutic index (MTC/MIC) of the compound No. 3 is 1000. As MIC of Methisazone (1-methylindole-2,3-dione 3-thiosemicarbazone), commercially available as an antiviral drug for small Pox virus (classified as the same Pox virus groups as vaccinia virus) infection, is 5 and its MTC is 20, its chemotherapeutic index is 4. Compared with these values, the compound No. 3 is proved to be 250 times as safe as Methisazone.

From this point of view the present compounds are superior to Methisazone, because their chemotherapeutic indexes (MTC/MIC) are remarkably higher than that of Methisazone as shown in Table I (Example 10).

Antiviral effects of the present compounds are also confirmed by in vivo experiments.

When mice are infected by intranasal infection of vaccinia virus, all mice in infected non-medicated control group die within 12 days, whereas all mice survive by an oral or subcutaneous treatment of 100 mg/kg of the present compound twice a day for 5 successive days as shown in Table II (Example 11). In addition, no side effects were observed in mice treated by these compounds.

Therefore the present compounds are superior to Methisazone as an antiviral agent. Thus the present compounds are epoch-making antiviral agents in terms of their remarkably effectiveness and very low toxicity.

As an antiviral agent, the compounds of the formula [I] may be administered alone or in the form of pharmaceutical compositions for veterinary medicine as hereinafter set forth.

The present compounds may be used in the form of pharmaceutical preparations appropriate for enteral or parenteral administration. Preferable excipients used therein are those which do not react with the compounds mentioned above, for example, water, gelatine, lactose, starch, stearic acid, magnesium stearate, talc, white petroleum jelly, vegitable oils, alcohol, benzyl alcohol, gums, polyalkylene glycols, or other known excipients for medicines. The pharmaceutical preparations may be in the form of tablets, powder, dragees (sugar coated tablets), capsules, suppositories, liquids, elixirs, emulsions, suspensions, syrups, chocolate, candy, waters, chewing gum or the like. If desired, they are sterilized and/or contain auxiliary substances such as preservatives, stabilisers, wetting agents, detergents or buffers. They may also additionally contain other therapeutically valuable substances (e.g. other antiviral agents, chemotherapeutic agents, antibiotics, anti-inflammatory agents, anti-pyretics, analgesics, enzyme preparations or the like).

The preparation of them are formulated by usual methods. They may be cojointly administered with a viral inhibitor such as interferon, interferon inducer or the like. The compositions and preparations should contain at least 0.1% of active component.

The compositions of this invention may be administered enterally, parenterally or in the form of nasal and oral aerosol spray. The compositions of this invention are also effective in resisting as well as combatting viral infections when administered topically to the site of the infection or potential infection in the form of ointments, salves, lotions, creams, sprays, drops, etc.

The amount of active component in such useful compositions or preparations in such that a suitable dosage of 0.2 mg to 200 mg/kg/day will be obtained.

The present compounds are useful for control of viral infections in the veterinary field, i.e. in domestic animals such as cattle, horse, pig, sheep, rabbit, etc. and in poultry such as chickens, turkey, quail, etc. and in pets such as dog, cat, canary, etc.

Dose of the compounds for a sufficient control of disease is dependent upon various factors such as kinds of compounds, kinds of combination drugs, species of viruses, degree of disease, species of animals, body weight, duration of treatment, administration route, etc. However, recommended daily dose is generally 0.2 to 400 mg/kg/day.

These compounds may be used systemically, more concretely, parenterally and non-parenterally, etc. and by a local application such as inhalation, topical application and dropping in the eye, etc., in the preparation form suitable for application such as liquid, ointment, powder, granule, mush, pellet, capsule, tablet, etc. by the addition of aforementioned solvent, additives, carriers, etc.

For veterinary use, these compounds may be used alone or in admixture with drinking water or feed in miscible form. In the latter application, compositions comprise one or more of the present compounds and other compounds, and one or more of additives such as water, ethanol, propylene glycol, skim milk, edible oil, syrup, cereals, surfactants, emulsifying agents, edible powder, commercially available animal feed, concentrates and feed additives.

The animal feed, concentrates and feed additives described above imply incomplete and complete animal feed containing minerals, vitamins, antioxidants, antibiotics, chemotherapeutics, growth promotors, coccidiostats, etc.

The novel quinazolinones of the aforesaid formula [II] can be prepared using a variety of known methods as described below.

One method for synthesis of the compounds of the formula [II], comprises reacting a compound of the formula,

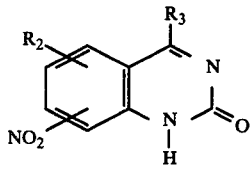

[III]

wherein $R_2$ and $R_3$ are as defined above, with a reactive ester of a compound of the formula,

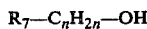

$R_7—C_nH_{2n}—OH$ [IV]

wherein n and $R_7$ are as defined above. The reaction may be carried out by reacting a compound of the formula [III] with a reactive ester of the compound of the formula [IV] in the presence of a condensing agent, or alternatively by treating the compound of the formula [III] with a condensing agent in a solvent to form a metal salt and then reacting the metal salt with the reactive ester of the compound of the formula [IV].

As the reactive ester of the compound of the formula [IV], there may be preferably used a hydrohalic acid ester such as chloride, bromide or iodide, or a sulfonic acid ester such as methanesulfonic acid ester, trichloromethanesulfonic acid ester or p-toluenesulfonic acid ester.

Suitable condensing agents include, for example, sodium hydride, potassium hydride, sodium amide, potassium amide, butyllithium, phenyllithium, sodium methylate, potassium methylate, sodium ethylate, potassium ethylate and mercuric chloride.

Suitable solvents include, for example, aromatic hydrocarbons such as benzene, toluene, xylene, monochlorobenzene; amides such as dimethylacetamide, diethylacetamide, dimethylformamide; ethers such as diethylether, tetrahydrofuran, dioxane; and dimethyl sulfoxide. The choice of the solvent may depend on the reactive ester and the condensing agent employed.

The reaction is generally effected at a temperature within the range between room temperature and the boiling point of the solvent used.

The reaction is generally accompanied by formation of the quinazoline derivatives of the formula,

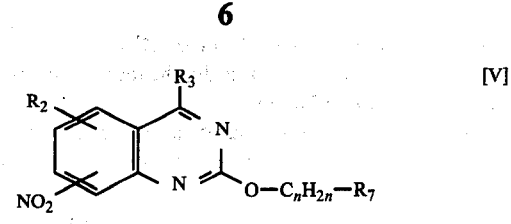

wherein $R_2$, $R_3$, n and $R_7$ are as defined above.

The separation of the desired compound of the formula [II] and the compound of the formula [V] may be effected using conventional techniques, for example, by chromatography or fractional crystallization.

Another method comprises reacting a compound of the formula,

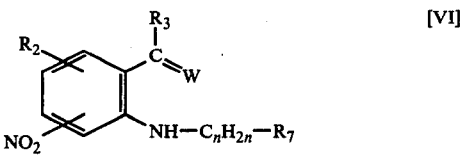

wherein $R_2$, $R_3$, n and $R_7$ are as defined above, and W is an oxygen atom or an imino group, with a carbamic acid ester, a carbamic acid halide, cyanic acid or a salt thereof or urea.

The reaction may be carried out by reacting a compound of the formula [VI] with a carbamic acid ester or a carbamic acid halide in the presence of a Lewis acid such as zinc chloride, otherwise with cyanic acid or a salt thereof or urea in the presence of a solvent such as acetic acid.

Examples of carbamic acid esters include methyl carbamate, ethyl carbamate, isopropyl carbamate and benzyl carbamate. Examples of carbamic acid halides include carbamyl chloride.

Examples of the salts of cyanic acid include sodium cyanate and potassium cyanate.

The reaction temperature may vary depending on the NCO group containing compound employed.

A further method comprises reacting a compound of the formula,

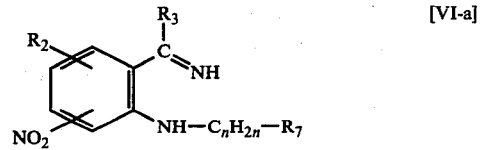

wherein $R_2$, $R_3$, n and $R_7$ are as defined above, with a carbonic acid derivative of the formula,

wherein Y and Z are each a chlorine atom, a lower alkoxy group, a benzyloxy group, a lower alkylthio group, a trichloromethyl group or a 1-imidazolyl group.

The reaction may be carried out in the presence or absence of an inert solvent and a basic condensing agent.

As the carbonic acid derivative of the formula [VII], there may be preferably used phosgene, methyl chlorocarbonate, ethyl chlorocarbonate, isopropyl chlorocarbonate, benzyl chlorocarbonate, ethyl chlorothiolformate, trichloroacetyl chloride, hexachloroacetone or 1,1'-carbonyldiimidazole.

Suitable solvents include, for example, benzene, toluene, xylene, chlorobenzene, pyridine, diethyl ether, isopropyl ether, tetrahydrofuran, dioxane, chloroform, dichloroethane, dimethylformamide and the like.

Suitable basic condensing agents include, for example, inorganic bases such as sodium hydroxide, potassium hydroxide, sodium carbonate or potassium carbonate, and tertiary amines such as triethylamine, N,N-dimethyl aniline or pyridine.

The reaction temperature may vary from about room temperature to the boiling point of the solvent, depending on the carbonic acid derivative employed.

A still further method for preparing the compounds of the formula [II], comprises reacting a compound of the formula,

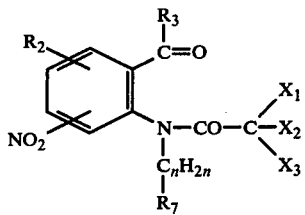

[VIII]

wherein $R_2$, $R_3$, n and $R_7$ are as defined above; and $X_1$, $X_2$ and $X_3$ are each a halogen atom, with ammonia.

The reaction may be carried out in the presence of a solvent or solvent mixture. Examples of the solvent include methanol, ethanol, isopropanol, tertiary-butanol, 2-ethoxyethanol, tetrahydrofuran, dioxane, acetone, pyridine, benzene, toluene, dimethylsulfoxide and dimethylformamide and mixture thereof. Ammonia is added to the reaction mixture as gaseous ammonia, alcoholic ammonia (e.g. methanolic or ethanolic ammonia), liquid ammonia or ammonium salt (e.g. ammonium acetate, ammonium formate, ammonium carbamate or ammonium succinate) which is generating ammonia during the reaction. The reaction generally proceeds at room temperature, and when desired, may be controlled appropriately by adopting a higher or lower temperature.

The starting compounds of the formula [VIII] are novel and also useful as intermediates for synthesis of other quinazoline derivatives. They can be conveniently obtained by reacting a compound of the formula,

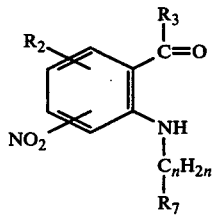

[VI-b]

wherein $R_2$, $R_3$, n and $R_7$ are as defined above, with a trihalogenoacetic acid, or a reactive derivative thereof, represented by the formula,

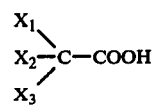

[IX]

wherein $X_1$, $X_2$ and $X_3$ are as defined above. Examples of the reactive derivatives of the trihalogenoacetic acid include, for example, acid halides and acid anhydrides.

The further alternative method for preparing the compounds of the formula [II], comprises contacting a compound of the formula,

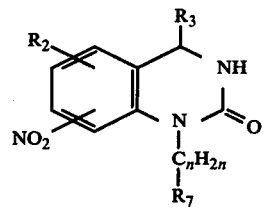

[X]

wherein $R_2$, $R_3$, n and $R_7$ are as defined above, with an oxidizing agent.

Suitable oxidizing agents include, for example, potassium permanganate, sodium permanganate, manganese dioxide, chromium trioxide, magnesium dioxide and sodium metaperiodate.

The reaction may be carried out in the presence of an inert solvent or solvent mixture.

Examples of the solvent include benzene, toluene, ether, tetrahydrofuran, dioxane, chloroform, carbon tetrachloride, acetone, ethanol, isopropanol, acetic acid, dimethylformamide, dimethyl sulfoxide and water and a mixture thereof.

The reaction is generally effected at a temperature within the range between about room temperature and the boiling point of the solvent employed.

The compound of the formula [X] can be obtained by reacting a compound of the formula,

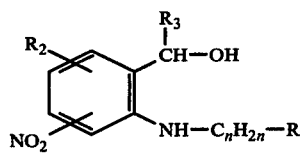

[XI]

wherein $R_2$, $R_3$, n and $R_7$ are as defined above, with a carbamic acid ester or carbamic acid halide, cyanic acid or a salt thereof or urea. The reaction may be effected by heating a compound of the formula [XI] with a carbamic acid ester (e.g. methyl carbamate, ethyl carbamate or benzyl carbamate) or a carbamic acid halide (e.g. carbamyl chloride) in the presence of a Lewis acid such as zinc chloride, otherwise with cyanic acid or a salt thereof (e.g. sodium cyanate or potassium cyanate) or urea in the presence of an acidic solvent such as acetic acid.

The thus obtained compounds of the formula [X] are also found to have potent antiviral activity.

The other method for preparing the compounds of the formula [II] comprises treating a quinazolinone derivative of the formula,

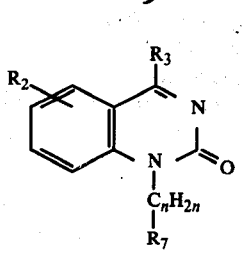

[XII]

wherein $R_2$, $R_3$, $R_7$ and n are as defined above, with a nitrating agent.

Examples of the nitrating agent include concentrated nitric acid, fuming nitric acid, mixed acid (e.g. nitric acid or fuming nitric acid in sulfuric acid, acetic acid, acetic anhydride, phosphoric acid or the like), potassium nitrate with sulfuric acid and cupric nitrate with acetic anhydride. The reaction may be carried out under cooling or heating to effect its desired control, depending upon the reactant and the nitrating agent employed. In some cases, dinitration may take place under vigorous reaction conditions.

According to the processes of the present invention, there are obtained, for example, the following nitroquinazolinone derivatives.

1-(2,3-Epoxypropyl)-4-phenyl-6-nitro-2(1H)-quinazolinone
1-(2,4-Epoxybutyl)-4-phenyl-6-nitro-2(1H)-quinazolinone
1-Tetrahydrofurfuryl-4-phenyl-6-nitro-2(1H)-quinazolinone
1-Tetrahydrofurfuryl-4-phenyl-8-nitro-2(1H)-quinazolinone
1-Tetrahydropyran-2-ylmethyl-4-phenyl-6-nitro-2-(1H)-quinazolinone
1-Tetrahydropyran-2-ylmethyl-4-(p-tolyl)-6-nitro-2(1H)-quinazolinone
1-Tetrahydropyran-2-ylmethyl-4-(o-chlorophenyl)-6-nitro-2(1H)-quinazolinone
1-Tetrahydrofuryl-4-phenyl-6-nitro-2(1H)-quinazolinone
1-Tetrahydropyran-2-yl-4-phenyl-6-nitro-2(1H)-quinazolinone
1-Tetrahydropyran-2-ylmethyl-4-(2-pyridyl)-6-nitro-2(1H)-quinazolinone
1-Tetrahydropyran-2-ylmethyl-4-(2-thienyl)-6-nitro-2(1H)-quinazolinone
1-(2-Tetrahydrothienylmethyl)-4-phenyl-6-nitro-2(1H)-quinazolinone
1-Furfuryl-4-phenyl-6-nitro-2(1H)-quinazolinone
1-(2-Thenyl)-4-phenyl-6-nitro-2(1H)-quinazolinone
1-(5-Methyl-2-thienylmethyl)-4-phenyl-6-nitro-2(1H)-quinazolinone
1-(1,4-Dioxacyclohexylmethyl)-4-phenyl-6-nitro-2(1H)-quinazolinone
1-(1,4-Benzodioxan-2-ylmethyl)-4-phenyl-6-nitro-2(1H)-quinazolinone
1-(2-Pyrrolidinylmethyl)-4-phenyl-6-nitro-2(1H)-quinazolinone
1-(2-Piperidylmethyl)-4-phenyl-6-nitro-2(1H)-quinazolinone
1-(3-Piperidylmethyl)-4-phenyl-6-nitro-2(1H)-quinazolinone
1-(4-Piperidylmethyl)-4-phenyl-6-nitro-2(1H)-quinazolinone
1-(1-Methyl-2-piperidylmethyl)-4-phenyl-6-nitro-2(1H)-quinazolinone
1-(1-Methyl-1,2,3,6-tetrahydro-4-pyridylmethyl)-4-phenyl-6-nitro-2(1H)-quinazolinone
1-(2-Pyrrolylmethyl)-4-phenyl-6-nitro-2(1H)-quinazolinone
1-(1-Methyl-2-pyrrolylmethyl)-4-phenyl-6-nitro-2(1H)-quinazolinone
1-(2-Pyridylmethyl)-4-phenyl-6-nitro-2(1H)-quinazolinone
1-(3-Pyridylmethyl)-4-phenyl-6-nitro-2(1H)-quinazolinone
1-(4-Pyridylmethyl)-4-phenyl-6-nitro-2(1H)-quinazolinone
1-(2-Pyrazinylmethyl)-4-phenyl-6-nitro-2(1H)-quinazolinone This invention is further disclosed in the following Examples of more preferred embodiments thereof, which are presented for the purpose of illustration and it is not intended to limit the scope of the invention.

EXAMPLE 1

To a suspension of 3.2 g of 4-phenyl-6-nitro-2(1H)-quinazolinone in 50 ml of dimethylformamide was added 0.7 g of 50% sodium hydride, and the mixture was stirred at 50° C. for 1 hour. Then, 3.96 g of tetrahydrofurfuryl bromide was added thereto and the resultant mixture was stirred at 100° C. for 7 hours. After cooling, the reaction mixture was poured into 300 ml of water and the resultant mixture was extracted with chloroform. The extract was washed with water and dried over anhydrous sodium sulfate. The solvent was removed under reduced pressure to give red oily residue. The residue was chromatographed on silica gel using chloroform as eluting solvent to obtain 1.9 g of 1-tetrahydrofurfuryl-4-phenyl-6-nitro-2(1H)-quinazolinone and 0.6 g of 2-tetrahydrofurfuryloxy-4-phenyl-6-nitroquinazoline. Each of them was recrystallized from ethanol, and the former gave pale yellow prisms, m.p. 151°–153° C. and the latter gave pale yellow scales, m.p. 135°–137° C.

EXAMPLE 2

The following compounds were obtained by the manner similar to that described in Example 1.
1-Tetrahydropyran-2-ylmethyl-4-phenyl-6-nitro-2(1H)-quinazolinone, m.p. 186°–187° C.
1-Furfuryl-4-phenyl-6-nitro-2(1H)-quinazolinone, m.p. 190°–190.5° C.
1-(1,4-Benzodioxan-2-ylmethyl)-4-phenyl-6-nitro-2(1H)-quinazolinone, m.p. 140°–141° C.
1-(2,3-Epoxypropyl)-4-phenyl-6-nitro-2(1H)-quinazolinone, m.p. 202.5°–203° C.
1-(2-Pyridylmethyl)-4-phenyl-6-nitro-2(1H)-quinazolinone, m.p. 175°–176° C.
1-(2-Thenyl)-4-phenyl-6-nitro-2(1H)-quinazolinone, m.p. 218°–219° C.
1-Tetrahydropyran-2-ylmethyl-4-(2-thienyl)-6-nitro-2(1H)-quinazolinone, m.p. 208.5°–209.5° C.

EXAMPLE 3

A mixture of 1.63 g of 2-tetrahydrofurfurylamino-5-nitrobenzophenone, 3.0 g of ethyl carbamate and 0.2 g of zinc chloride was heated at 190° C. (oil bath temperature) for 2 hours. After cooling, the reaction mixture was dissolved in chloroform and the insoluble material was filtered off. The chloroform solution was washed successively with dilute hydrochloric acid and water, and dried over anhydrous sodium sulfate. The solvent was removed under reduced pressure and the residue was washed with ether. The insoluble product was collected by filtration and dried to give 1-tetrahydrofurfuryl-4-phenyl-6-nitro-2(1H)-quinazolinone, m.p. 150°–152° C.

EXAMPLE 4

To a mixture of 1.63 g of 2-tetrahydrofurfurylamino-5-nitrobenzophenonimine, 6 ml of triethylamine and 50 ml of benzene was added dropwise at 5°–10° C. with cooling 35 ml of a 10% phosgene solution in benzene. The resulting mixture was stirred at room temperature for 2 hours and then concentrated to dryness under reduced pressure. To the residue were added 50 ml of a dilute aqueous sodium carbonate solution and 50 ml of chloroform and the residue was dissolved with moderate stirring. The organic layer was separated and the aqueous layer was further extracted with chloroform. The extracts were combined and washed with water, and dried over anhydrous sodium sulfate. The solvent was removed under reduced pressure. The residue was chromatographed on silica gel using chloroform as eluting solvent to obtain 1-tetrahydrofurfuryl-4-phenyl-6-nitro-2(1H)-quinazolinone, m.p. 150°–152° C.

EXAMPLE 5

A mixture of 1.63 g of 2-tetrahydrofurfurylamino-5-nitrobenzophenonimine, 1 ml of ethyl chlorocarbonate and 20 ml of benzene was refluxed for 3 hours. After cooling, the reaction mixture was washed with water and dried over anhydrous sodium sulfate. The solvent was removed under reduced pressure and the residue was chromatographed on silica gel using chloroform as eluting solvent to give 1-tetrahydrofurfuryl-4-phenyl-6-nitro-2(1H)-quinazolinone, m.p. 150°–151° C.

EXAMPLE 6

Using a procedure similar to that described in Example 5, but replacing ethyl chlorocarbonate by 1,1'-carbonyldiimidazole, there was obtained 1-tetrahydrofurfuryl-4-phenyl-6-nitro-2(1H)-quinazolinone, m.p. 150°–151° C.

EXAMPLE 7

A mixture of 2.36 g of 2-(N-tetrahydrofurfuryltrichloroacetamido)-5-nitrobenzophenone, 2.4 g of ammonium acetate, 0.5 g of triethylamine and 30 ml of tertiary butanol was stirred under reflux for 10 hours. Then the solvent was removed and water was added to the residue. The resulting mixture was extracted with chloroform and the extract was washed successively with dilute ammonia water and water, and dried over anhydrous sodium sulfate. The solvent was removed under reduced pressure. The residue was washed with ether and the insoluble product was collected by filtration and dried to give 1-tetrahydrofurfuryl-4-phenyl-6-nitro-2(1H)-quinazolinone, m.p. 150°–152° C.

EXAMPLE 8

A mixture of 3.42 g of 2-(2-thenylamino)-5-nitrobenzhydrol, 6 g of ethyl carbamate and 0.5 g of zinc chloride was heated at 180° C. (bath temperature) for 2 hours. After cooling, the reaction mixture was dissolved in chloroform and the chloroform solution was washed with water and dried over anhydrous sodium sulfate. The solvent was removed under reduced pressure to give 1-(2-thenyl)-4-phenyl-6-nitro-3,4-dihydro-2(1H)-quinazolinone.

Subsequently, the compound above obtained was dissolved in 80 ml of dioxane and a solution of 1.6 g of potassium permanganate in 30 ml of water was added dropwise thereto. After the mixture was stirred at room temperature for 2 hours, a few drops of formic acid was added. The resulting brown precipitate was filtered off and the filtrate was concentrated under reduced pressure. The residue was dissolved in chloroform and the chloroform layer was washed with water and dried over anhydrous sodium sulfate. The solvent was removed under reduced pressure. The residue was crystallized from ethanol-chloroform to give 1-(2-thenyl)-4-phenyl-6-nitro-2(1H)-quinazolinone, m.p. 219°–220° C.

EXAMPLE 9

To a solution of 3.13 g of 1-(2-pyridylmethyl)-4-phenyl-2(1H)-quinazolinone in 10 ml of concentrated sulfuric acid was added dropwise a solution of 1 g of potassium nitrate in 3 ml of concentrated sulfuric acid with cooling by an ice bath. The resulting mixture was stirred at room temperature for 3 hours and then poured onto cracked ice. The precipitate was collected by filtration, washed successively with water and ammonia water and dried to give 1-(2-pyridylmethyl)-4-phenyl-6-nitro-2(1H)-quinazolinone. Recrystallization from chloroform gave colorless fine crystals, m.p. 175°–176° C.

EXAMPLE 10

Effects on vaccinia virus multiplication in chick embryo fibroblast cell culture.

General procedure of two fold tube dilution method was employed. Monolayer chick embryo fibroblast cells were prepared by general procedure, i.e., trypsinization of 10 to 11 days old chick embryo and then 3 days' incubation in lactalbumin Hanks' medium containing 5% calf serum at 37° C. in stoppered tube. Then growth medium was discarded and $1.1 \times 10^4$ plaque forming units (PFU) of vaccinia virus IHD strain per tube were challenged.

Thus virus challenged monolayer cell sheets were replaced with lactalbumin Eagle's medium containing 2% calf serum and appropriate concentration of test compounds. After 3 days' incubation at 37° C. cytopathogenic effects (CPE) were observed microscopically. Antiviral activities of the test compounds were expressed as the minimum inhibitory concentration (MIC, μg/ml) and their toxic effects as the minimum toxic concentration (MTC, μg/ml).

These results with a number of representative compounds are shown in Table I.

All compounds listed in Table I are superior to Methisazone considering from their chemotherapeutic indexes (MTC/MIC).

Table I.

| Compound No. shown in Table VIII | MIC[1] (μg/ml) | MTC[2] (μg/ml) | Chemotherapeutic index (MTC/MIC) |
|---|---|---|---|
| 1 | 0.1 | 100 | 1000 |
| 2 | 0.1 | 100 | 1000 |
| 3 | 0.1 | 100 | 1000 |
| 4 | 0.1 | 100 | 1000 |
| 5 | 0.2 | >100 | >500 |
| 6 | 0.2 | 50 | 250 |
| 7 | 0.2 | >100 | >500 |
| 8 | 0.25 | 5 | 20 |
| 9 | 0.25 | 5 | 20 |
| 10 | 0.4 | >100 | >250 |
| 11 | 0.6 | 25 | 40 |

*Effects on vaccinia virus multiplication in chick embryo fibroblast cell culture*

Table I.-continued

Effects on vaccinia virus multi-
plication in chick embryo fibroblast
cell culture

| Compound No. shown in Table VIII | MIC*1 (μg/ml) | MTC*2 (μg/ml) | Chemotherapeutic index (MTC/MIC) |
| --- | --- | --- | --- |
| 12 | 0.6 | 50 | 80 |
| 13 | 1.0 | 100 | 100 |
| 14 | 1.25 | >100 | >80 |
| 15 | 5.0 | >100 | >20 |
| 16 | 5.0 | >100 | >20 |
| 17 | 5.0 | >100 | >20 |
| 18 | 5.0 | >100 | >20 |
| 19 | 5.0 | >100 | >20 |
| 20 | 5.0 | 50 | 10 |
| 21 | 5.0 | 50 | 10 |
| 22 | 5.0 | 50 | 10 |
| Methisazone | 5.0 | 20 | 4 |

Note)
cells* chick embryo fibroblast cells
virus: vaccinia virus IHD strain, 1.1 × 10⁴ PFU/tube
observation: by cytopathogenic effect (CPE) after 3 days'incubation at 37° C, microscopically
*1MIC: Minimum inhibitory concentration
*2MTC: Minimum toxic concentration

EXAMPLE 11

Therapeutic effects on experimental vaccinia infection in mice.

Three weeks old male mice of ICR strain were employed. 2.2 × 10⁴ plaque forming units (PFU) of vaccinia virus IHD strain were challenged intranasally to each animal.

Each animal was treated −2, 4, 16, 28, 40, 52, 64, 76, 88 and 100 hours after infection orally or subcutaneously. Mice were observed for 12 days after infection.

The results are shown as survival rates in Table II.

The compounds of the present invention are not only very effective but also show no side effects. For example, acute toxicity of the present compound by the intraperitoneal injection in mice is remarkably lower than Methisazone as shown in Table III.

Severe gastro-duodenal hemorrhage and intestinal ulceration were observed in dead mice to which Methisazone has been administered. On the contrary, in the case of the present compound neither hemorrhage nor ulceration were detected.

Table II.

Therapeutic effects on experi-
mentally vaccinial infection
in mice

| Compound No. | Survival rate (%) | |
| --- | --- | --- |
|  | PO | SC |
| 3 | 100 | 100 |
| 5 | — | 100 |
| 11 | — | 100 |
| 14 | — | 100 |
| Methisazone | 100 | 100 |
| infected non-medicated control | 0 | 0 |

Note)
animals: 3 weeks old male mice (ICR strain) 8/group
virus: vaccinia virus IHD strain
challenge: 2.2 × 10⁴ PFU per animal, intranasally
treatment: 100 mg/kg; orally (PO) or subcutaneously (SC); − 2, 4, 16, 28, 40, 52, 64, 76, 88 & 100 hours after virus challenge
observation period: for 12 days after infection Table III.

Comparison of the present compound
with Methisazone in acute toxicity
in mice

| Dose (mg/kg) | No. of survivors/ No. of tested | | |
| --- | --- | --- | --- |
|  | Compound No. | | |
|  | 5 | 14 | Methisazone |
| 1000 | 5/5 | 5/5 | 3/5 |
| 2000 | 4/5 | 4/5 | 0/5 |

Note)
animals: male mice weighing 17 to 20 g of ddN strain
administration: intraperitoneally, suspension in 0.5% carboxymethyl cellulose
observation period: 7 days after an administration

EXAMPLE 12

Effects on herpes simplex virus multiplication in chick embryo fibroblast cell culture.

A general procedure of plaque-reduction method was employed. Monolayers of chick embryo fibroblast cells were prepared by a general procedure, i.e., trypsinization of 10 day old chick embryo and then 2 days' incubation in Eagle's minimum essential medium (Eagle's MEM) containing a 5% calf serum at 37° C. in a plaque tube. Then, growth medium was discarded and about 100 plaque forming units (PFU) of herpes simplex virus HF strain per plaque tube were challenged. The virus challenged monolayer cell sheets were overlayed with 1% bactoagar dissolved in YLE medium (Eagle's medium containing yeast extracts and lactoalbumin) containing a 2% calf serum and test compounds in appropriate concentration. After 4 day's incubation at 37° C., the number of plaques was counted and compared with the controlled plaque tube without test compounds. Antiviral activities of the tested compounds were expressed as percentage inhibition of occurrences of plaques.

These results are shown in Table IV.

Table IV.

Effects on herpes simplex virus multi-
plication in chick embryo fibroblast
cell culture

| Compound No. | Concentration (μg/ml) | Average number of plaques | Percentage in inhibition (%) |
| --- | --- | --- | --- |
| 5 | 5 | 9 | 80 |
| 9 | 5 | 2 | 96 |
| Non-medicated control | 0 | 45 | — |

Note)
cells: chick embryo fibroblast cells
virus: herpes simplex virus HF strains
observation: by counting the number of plaques after 4 days' incubation at 37° C.

EXAMPLE 13

Effects on adeno virus multiplication in human embryonic lung filbroblast cell culture.

A general procedure of measuring haemagglutinating titre of virus was embloyed. Monolayers of human embryonic lung fibroblast T16L strain was maintained in Eagle's MEM containing a 10% calf serum at 37° C. Then, growth medium was discarded and adeno virus type 8 Kanehisa strain was challenged. After 1.5 hrs. of the challenge, medium was changed by Eagle's MEM containing a 2% calf serum and test compounds in appropriate concentration. On 5th day after the infection, cells were harvested and disrupted by three freezings and thawings and centrifuged at 3,000 rpm for 3 minutes. The supernatant was employed as a source of haemagglutinating reaction. The supernatant was two-fold diluted successively with phosphate buffered saline and thereto was added equal volume of 1% rat blood cells freshly prepared by sacrifice of male rats (Sprangue-Dawley strain). After the mixture was incubated at 37° C. for 5 hrs., the haemagglutinating titre was determined as the maximum dilution enough to agglutinate rat red blood cells. Antiviral activities of the tested compounds were expressed as reduction of haemagglutinating titre.

These results are shown in Table V.

Table V.

Effects on adeno virus multiplication in human embryonic lung cell culture

| Compound No. | Concentration (g/ml) | Haemagglutinating titre |
|---|---|---|
| 3 | 40 | 32 |
| 5 | 40 | 64 |
| 14 | 40 | 32 |
| Non-medicated control | 0 | 512 |

Note)
cells: human embryonic lung cell
virus: adeno virus type 8 Kanehisa strain

EXAMPLE 14

Effects on parainfluenza virus multiplication in chick embryo fibroblast cell culture.

A general procedure of haemagglutinating titration was employed. Monolayers of chick embryo fibroblast cells were prepared by the same procedure as described in Example 12. Parainfluenza virus type 1, haemagglutinating virus of Japan (HVJ), so called Sendai virus was challenged on 3rd day monolayer cell sheet. Thus virus challenged monolayer cell sheets were replaced with Eagle's MEM containing a 2% calf serum and test compounds in appropriated concentration. After 2 days' incubation at 37° C., the cells were harvested, disrupted by freezing and thawing and centrifuged. The haemagglutinating titre of the supernatant was assayed using 1% guinea pig red blood cell as usual. Antiviral activities of the tested compounds were expressed as reduction of haemagglutinating titre.

These results are shown in Table VI.

Table VI.

Effects on parainfluenza virus type 1 in chick embryo fibroblast cell culture

| Compound No. | Concentration (μg/ml) | Haemagglutinating titre |
|---|---|---|
| 2 | 12.5 | 4 |
|   | 25 | 2 |
| 5 | 12.5 | 4 |
|   | 25 | < 2 |
| Non-medicated control | 0 | 32 |

Note)
cells: chick embryo fibroblast cell
virus: parainfluenza virus type 1, Sendai virus

EXAMPLE 15

Therapeutic effects on experimental influenza virus infection in mice.

Three weeks old male mice of ICR strain (8/group) were employed. Influenza virus NWS strain (32–64 HA titre) or FM-1 strain (128–256 HA titre) was challenged intranasally to each animal. Each animal was treated −3, 3, 20, 27, 44, 51, 68 and 77 hours after infection subcutaneously. Mice were observed for 14 days after infection. These results are shown as survival rates in Table VII.

Table VII.

Effects on influenza virus infection in mice

| Challenged virus strain | Compound No. | Dose (mg/kg) | Survival rate |
|---|---|---|---|
| NWS strain | 5 | 50 | 6/8 |
|  | " | 10 | 4/8 |
|  | Non-mediated control | — | 1/8 |
| FM-1 strain | 5 | 200 | 4/8 |
|  | Non-mediated control | — | 0/8 |

Table VIII.

Chemical structures of the compounds listed in Table I to VII

| Compound No. | $R_1$ | $NO_2$— position | $R_2$ | $R_3$ |
|---|---|---|---|---|
| 1 | —$CH_2$—(cycloheptyl, H) | 6- | H | phenyl |
| 2 | (cyclohexyl, H) | " | " | " |
| 3 | —$CH_2$—(cyclohexyl, H) | " | " | " |
| 4 | —$CH_2$—(cyclooctyl, H) | " | " | " |
| 5 | —$CH_2$—(tetrahydropyranyl, O) | " | " | " |
| 6 | —$CH_2$—(pyridyl, N) | " | " | " |
| 7 | —$CH_2$—(cyclobutyl) | " | " | " |
| 8 | —$CH_2$—(chlorophenyl, Cl) | " | " | " |
| 9 | —$CH_2$—(methylcyclohexyl, $CH_3$) | " | " | " |
| 10 | —$CH_2$—(tetrahydropyranyl, O) | " | " | thienyl (S) |
| 11 | —$CH_2$—(cyclohexyl) | " | " | phenyl |

What is claimed is:

1. A nitroquinazolinone represented by the formula

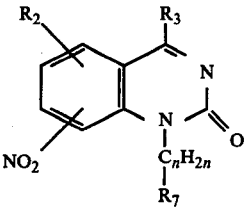

wherein $R_2$ is hydrogen, $R_3$ is phenyl or thienyl, $R_7$ is furyl, thien-2-yl, pyridyl, tetrahydrofuryl or tetrahydropyran-2-yl; and n is an integer of 1.

2. The compound of claim 1 which is 1-furfuryl-4-phenyl-6-nitro-2(1H)-quinazolinone.

3. The compound of claim 1 which is 1-tetrahydrofurfuryl-4-phenyl-6-nitro-2(1H)-quinazolinone.

4. The compound of claim 1 which is 1-tetrahydropyran-2-ylmethyl-4-phenyl-6-nitro-2(1H)-quinazolinone.

5. The compound of claim 1 which is 1-tetrahydropyran-2-ylmethyl-4-(2-thienyl)-6-nitro-2(1H)-quinazolinone.

6. The compound of claim 1 which is 1-(2-thenyl)-4-phenyl-6-nitro-2(1H)-quinazolinone.

7. The compound of claim 1 which is 1-(2-pyridylmethyl)-4-phenyl-6-nitro-2(1H)-quinazolinone.

* * * * *